(12) United States Patent
Brady et al.

(10) Patent No.: US 9,217,008 B1
(45) Date of Patent: Dec. 22, 2015

(54) ANTICANCER AGENTS OF THE ANTHRACYCLIN FAMILY

(71) Applicants: Sean Brady, New York, NY (US); Hahk-Soo Kang, New York, NY (US)

(72) Inventors: Sean Brady, New York, NY (US); Hahk-Soo Kang, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/327,597

(22) Filed: Jul. 10, 2014

Related U.S. Application Data

(60) Provisional application No. 61/844,617, filed on Jul. 10, 2013.

(51) Int. Cl.
*C07H 15/252* (2006.01)

(52) U.S. Cl.
CPC .................................. *C07H 15/252* (2013.01)

(58) Field of Classification Search
None
See application file for complete search history.

(56) References Cited

FOREIGN PATENT DOCUMENTS

FR           2543545      * 10/1984

OTHER PUBLICATIONS

Hahk-Soo Kang, Sean F Brady "Arimetamycin A: improving clinically relevant families of natural products through sequence-guided screening of soil metagenomes."Angew Chem Int Ed Engl Oct. 3, 2013;52(42):11063-7. Epub Sep. 3, 2013.

* cited by examiner

*Primary Examiner* — Traviss C McIntosh, III
(74) *Attorney, Agent, or Firm* — Heslin, Rothenberg, Farley & Mesiti P.C.

(57) ABSTRACT

Anthracyclin compounds of the general structure:

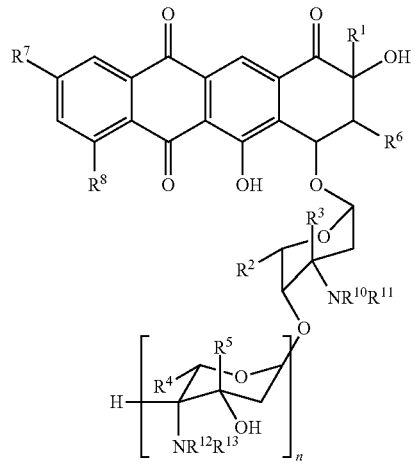

are disclosed. In these compounds $R^1$ is methyl, acetyl or hydroxyacetyl; $R^2$-$R^5$ and $R^{10}$-$R^{13}$ are independently H or methyl; $R^6$ $R^7$ and $R^8$ are independently H, OH or $OCH_3$; and n is zero or one. The compounds are useful for treating cancer.

18 Claims, 1 Drawing Sheet

Gene annotation table of the eDNA clone AZ129

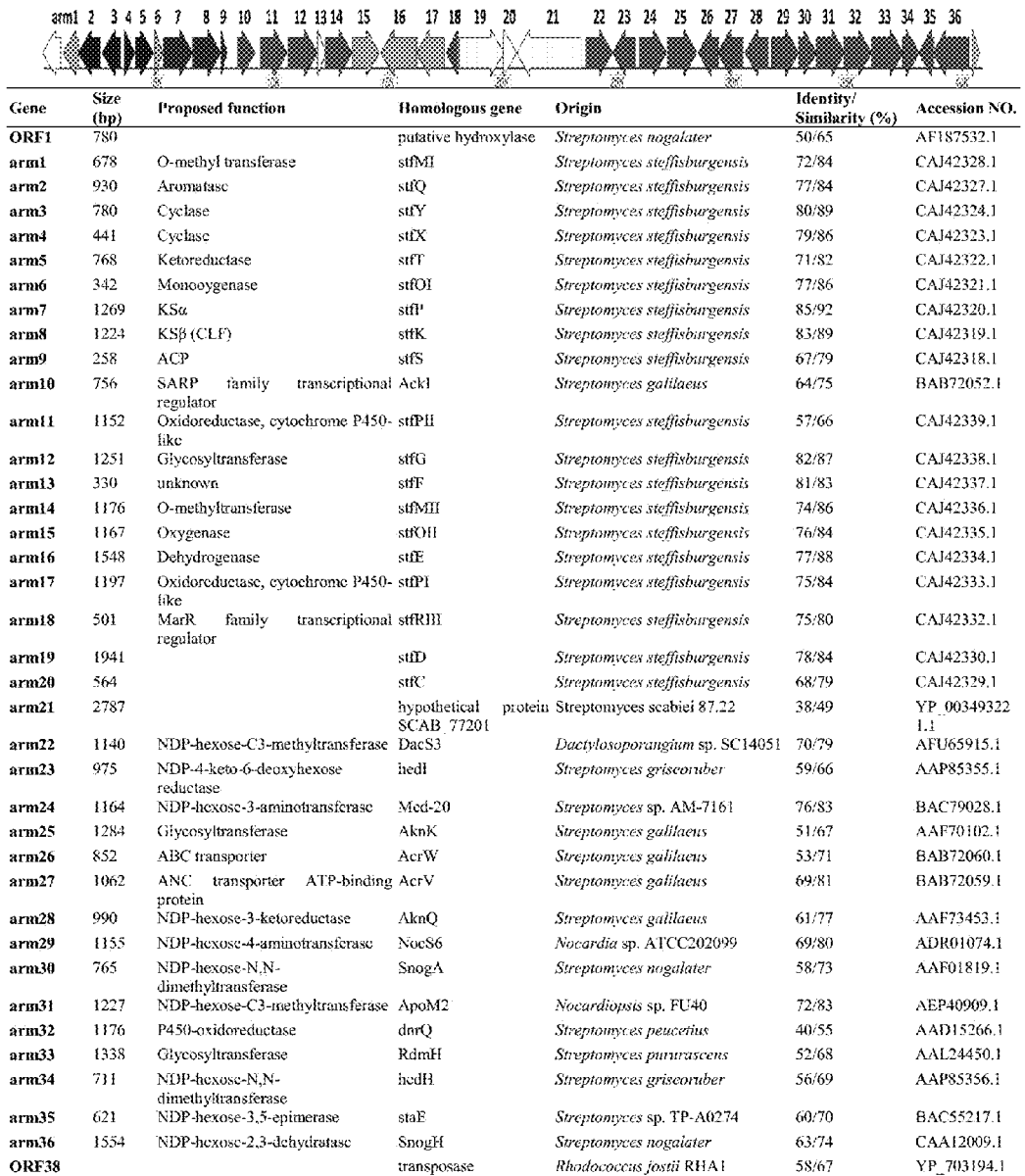

| Gene | Size (bp) | Proposed function | Homologous gene | Origin | Identity/Similarity (%) | Accession NO. |
|---|---|---|---|---|---|---|
| ORF1 | 780 | | putative hydroxylase | Streptomyces nogalater | 50/65 | AF187532.1 |
| arm1 | 678 | O-methyl transferase | stfMI | Streptomyces steffisburgensis | 72/84 | CAJ42328.1 |
| arm2 | 930 | Aromatase | stfQ | Streptomyces steffisburgensis | 77/84 | CAJ42327.1 |
| arm3 | 780 | Cyclase | stfY | Streptomyces steffisburgensis | 80/89 | CAJ42324.1 |
| arm4 | 441 | Cyclase | stfX | Streptomyces steffisburgensis | 79/86 | CAJ42323.1 |
| arm5 | 768 | Ketoreductase | stfT | Streptomyces steffisburgensis | 71/82 | CAJ42322.1 |
| arm6 | 342 | Monooygenase | stfOI | Streptomyces steffisburgensis | 77/86 | CAJ42321.1 |
| arm7 | 1269 | KSα | stfP | Streptomyces steffisburgensis | 85/92 | CAJ42320.1 |
| arm8 | 1224 | KSβ (CLF) | stfK | Streptomyces steffisburgensis | 83/89 | CAJ42319.1 |
| arm9 | 258 | ACP | stfS | Streptomyces steffisburgensis | 67/79 | CAJ42318.1 |
| arm10 | 756 | SARP family transcriptional regulator | AckI | Streptomyces galilaeus | 64/75 | BAB72052.1 |
| arm11 | 1152 | Oxidoreductase, cytochrome P450-like | stfPII | Streptomyces steffisburgensis | 57/66 | CAJ42339.1 |
| arm12 | 1251 | Glycosyltransferase | stfG | Streptomyces steffisburgensis | 82/87 | CAJ42338.1 |
| arm13 | 330 | unknown | stfF | Streptomyces steffisburgensis | 81/83 | CAJ42337.1 |
| arm14 | 1176 | O-methyltransferase | stfMII | Streptomyces steffisburgensis | 74/86 | CAJ42336.1 |
| arm15 | 1167 | Oxygenase | stfOII | Streptomyces steffisburgensis | 76/84 | CAJ42335.1 |
| arm16 | 1548 | Dehydrogenase | stfE | Streptomyces steffisburgensis | 77/88 | CAJ42334.1 |
| arm17 | 1197 | Oxidoreductase, cytochrome P450-like | stfPI | Streptomyces steffisburgensis | 75/84 | CAJ42333.1 |
| arm18 | 501 | MarR family transcriptional regulator | stfRIII | Streptomyces steffisburgensis | 75/80 | CAJ42332.1 |
| arm19 | 1941 | | stfD | Streptomyces steffisburgensis | 78/84 | CAJ42330.1 |
| arm20 | 564 | | stfC | Streptomyces steffisburgensis | 68/79 | CAJ42329.1 |
| arm21 | 2787 | | hypothetical protein SCAB_77201 | Streptomyces scabiei 87.22 | 38/49 | YP_00349322.1 |
| arm22 | 1140 | NDP-hexose-C3-methyltransferase | DacS3 | Dactylosporangium sp. SC14051 | 70/79 | AFU65915.1 |
| arm23 | 975 | NDP-4-keto-6-deoxyhexose reductase | hedI | Streptomyces griseoruber | 59/66 | AAP85355.1 |
| arm24 | 1164 | NDP-hexose-3-aminotransferase | Med-20 | Streptomyces sp. AM-7161 | 76/83 | BAC79028.1 |
| arm25 | 1284 | Glycosyltransferase | AknK | Streptomyces galilaeus | 51/67 | AAF70102.1 |
| arm26 | 852 | ABC transporter | AcrW | Streptomyces galilaeus | 53/71 | BAB72060.1 |
| arm27 | 1062 | ANC transporter ATP-binding protein | AcrV | Streptomyces galilaeus | 69/81 | BAB72059.1 |
| arm28 | 990 | NDP-hexose-3-ketoreductase | AknQ | Streptomyces galilaeus | 61/77 | AAF73453.1 |
| arm29 | 1155 | NDP-hexose-4-aminotransferase | NocS6 | Nocardia sp. ATCC202099 | 69/80 | ADR01074.1 |
| arm30 | 765 | NDP-hexose-N,N-dimethyltransferase | SnogA | Streptomyces nogalater | 58/73 | AAF01819.1 |
| arm31 | 1227 | NDP-hexose-C3-methyltransferase | ApoM2 | Nocardiopsis sp. FU40 | 72/83 | AEP40909.1 |
| arm32 | 1176 | P450-oxidoreductase | dnrQ | Streptomyces peucetius | 40/55 | AAD15266.1 |
| arm33 | 1338 | Glycosyltransferase | RdmH | Streptomyces purpurascens | 52/68 | AAL24450.1 |
| arm34 | 711 | NDP-hexose-N,N-dimethyltransferase | hedH | Streptomyces griseoruber | 56/69 | AAP85356.1 |
| arm35 | 621 | NDP-hexose-3,5-epimerase | staE | Streptomyces sp. TP-A0274 | 60/70 | BAC55217.1 |
| arm36 | 1554 | NDP-hexose-2,3-dehydratase | SnogH | Streptomyces nogalater | 63/74 | CAA12009.1 |
| ORF38 | | | transposase | Rhodococcus jostii RHA1 | 58/67 | YP_703194.1 |

ANTICANCER AGENTS OF THE ANTHRACYCLIN FAMILY

CROSS-REFERENCE TO RELATED APPLICATIONS

This application claims priority to U.S. Provisional Patent Application No. 61/844,617, filed Jul. 10, 2013, which is incorporated herein by reference in its entirety.

FEDERALLY SPONSORED RESEARCH

The following invention was made with Government support under contract number NIH GM077516. The Government has certain rights in this invention.

FIELD OF THE INVENTION

The invention relates to compounds in the anthracyclin family that inhibit the growth of neoplastic cells (including multidrug resistant cells). These compounds are useful to treat various cancers.

BACKGROUND OF THE INVENTION

Anthracyclines rank among the most effective anti-cancer drugs ever developed. The first anthracyclines were isolated from *Streptomyces peucetius* early in the 1960s and were named doxorubicin (DOX) and daunorubicin (DNR). DOX and DNR both consist of an aglyconic and a sugar moiety. The aglycone consists of a tetracyclic ring with adjacent quinone-hydroquinone groups in rings C-B, a methoxy substituent at C-4 in ring D, and a short side chain at C-9 with a carbonyl at C-13. The sugar, called daunosamine, is attached by a glycosidic bond to the C-7 of ring A and consists of a 3-amino-2,3,6-trideoxy-L-fucosyl moiety. Daunorubicin has the structure:

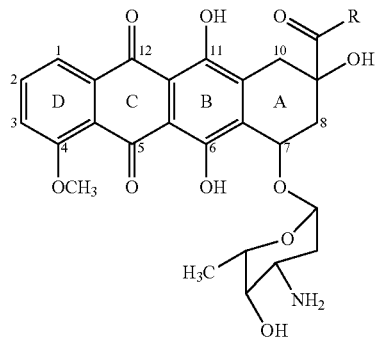

The only difference between DOX and DNR is that the side chain at C-9 of DOX is a hydroxyacetyl, whereas that of DNR is acetyl. This difference is reflected in the spectrum of activity of DOX and DNR. Whereas DOX is an established component of treatment of breast cancer, childhood solid tumors, soft tissue sarcomas, and aggressive lymphomas, DNR shows activity in acute lymphoblastic or myeloblastic leukemias.

Unfortunately, the clinical use of both DOX and DNR is severely limited by the development of resistance in tumor cells and toxicity in healthy tissues. The toxicity to healthy tissues is manifested in cardiomyopathy and congestive heart failure (CHF). To avoid the latter, the maximum recommended cumulative doses of DNR and DOX have been generally recommended not to exceed 600 mg/m². Chemists have spent decades identifying and/or synthesizing novel anthracyclines, looking for compounds superior to DOX or DNR in terms of activity and/or cardiac tolerability. The search has resulted in thousands of analogs, but only a handful have reached the stage of clinical development and approval, and the search for anthracyclins with improved specificity, activity and therapeutic ratio continues.

SUMMARY OF THE INVENTION

In one aspect, the invention relates to anthracyclins having the structure:

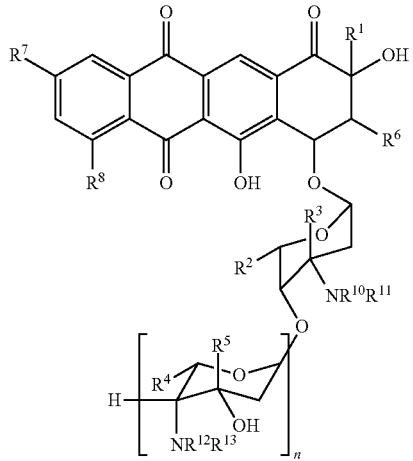

wherein
$R^1$ is chosen from methyl, acetyl and hydroxyacetyl;
$R^2$-$R^5$ and $R^{10}$-$R^{13}$ are independently chosen from H and methyl;
$R^6$, $R^7$ and $R^8$ are independently chosen from H, OH and $OCH_3$; and
n is zero or one.

In another aspect, the invention relates to methods for treating cancer comprising exposing the cell to a compound described herein.

In another aspect, the invention relates to pharmaceutical compositions comprising a pharmaceutically acceptable carrier and a compound described herein.

BRIEF DESCRIPTION OF THE DRAWING

FIG. 1 is a Gene annotation table of the eDNA clone AZ129.

DETAILED DESCRIPTION OF THE INVENTION

In its most basic aspects, the invention relates to compounds having the structure:

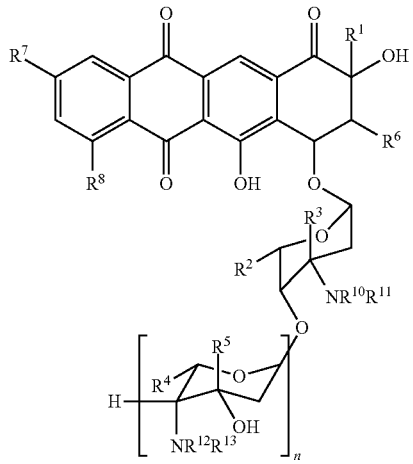

and to methods of using the compounds and pharmaceutical compositions containing compounds.

In some embodiments, $R^7$ is OH; in others $R^7$ is $OCH_3$. In some embodiments, $R^6$ is H; in others, $R^6$ is $OCH_3$. In some embodiments, $R^8$ is H; in others, $R^8$ is OH. In some embodiments, $R^8$ is OH, $R^6$ is $OCH_3$ and $R^7$ is $OCH_3$. In some embodiments, n is one and all of $R^2$-$R^5$ and $R^{10}$-$R^{13}$ are methyl. In some embodiments, $R^1$ is methyl; in others $R^1$ is acetyl and in still others $R^1$ is hydroxyacetyl.

Throughout this specification the terms and substituents retain their definitions.

As used herein, and as would be understood by the person of skill in the art, the recitation of "a compound"—unless expressly further limited—is intended to include salts of that compound. Thus, for example, the recitation "a compound of formula"

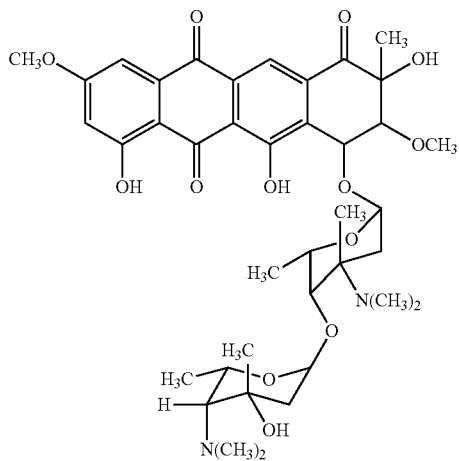

as depicted above, would include salts in which the nitrogen of one or both of the amino sugars is protonated and is paired with any counterion. In a particular embodiment, the term "compound" refers to the compound or a pharmaceutically acceptable salt thereof. The term "pharmaceutically acceptable salt" refers to salts prepared from pharmaceutically acceptable non-toxic acids or bases including inorganic acids and bases and organic acids and bases. The compounds of the present invention are basic, and salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Further pharmaceutically acceptable salts include, when appropriate, sulfonate and phosphonate anions attached to alkyl having from 1 to 20 carbon atoms.

Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula X is intended to encompass both of the pure enantiomers of that pair:

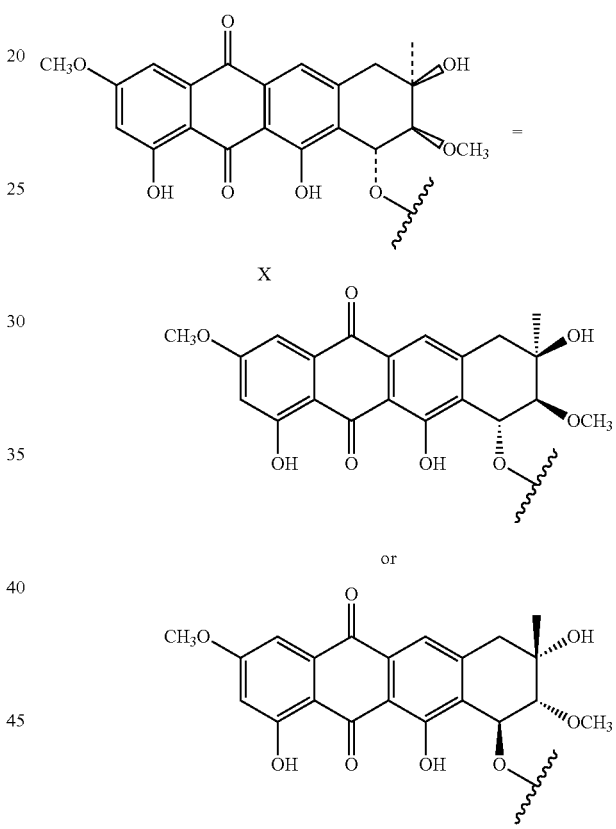

The chemical diversity encoded by natural microbial communities has been significantly underexplored due to limitations associated with the inability to culture the majority of environmental bacteria and the silencing of biosynthetic pathways under laboratory conditions. Soils contain thousands of unique bacterial species, which potentially harbor tens of thousands of functionally unexplored natural product biosynthetic gene clusters. With the development of metagenomic cloning methods, it is possible to use DNA extracted directly from soil (environmental DNA, eDNA) to construct libraries that capture the enormous biosynthetic diversity present in soil environments. These libraries provide a means of functionally examining unexplored soil biosynthetic gene clusters and are, therefore, resources for sequence-guided natural product discovery programs. We have used these libraries to identify novel members of clinically relevant natural product families with potentially improved biological activities.

We disclose herein a natural product sequence-tag driven approach to guide the discovery of an anthracycline-based aromatic polyketide genus that shows improved in vitro antiproliferative activity compared to the natural product anthracyclines that are currently in clinical use.

Aromatic polyketides comprise a large class of structurally and functionally diverse bacterial natural products. The biosyntheses of these metabolites, although differing in detail, all originate with the production of a polyacetate precursor by a conserved minimal polyketide synthase (min-PKS) that is composed of three proteins [acyl carrier protein (ACP), β-ketoacyl synthase alpha ($KS_\alpha$), β-ketoacyl synthase beta ($KS_\beta$)]. $KS_\alpha$ and $KS_\beta$ genes clade into groups that correlate strongly with the specific aromatic polyketide structural classes that are encoded by the gene clusters in which they reside. To this end, cosmid DNA isolated from four previously archived and arrayed soil eDNA mega-libraries [California (AB), Utah (UT), Arizona (AZ), Texas (TX)] was screened by PCR using min-PKS specific degenerate primers. Each soil mega-library contains more than 10,000,000 clones arrayed as sub-libraries of 5,000 unique clones to facilitate PCR screening and downstream recovery of individual clones of interest. PCR amplicons generated during the screening of individual sub-libraries were sequenced and phylogenetically compared to the corresponding $KS_\beta$ fragments from biosynthetic gene clusters known to encode for clinically relevant polyketide families. eDNA-derived $KS_\beta$ sequences that fell into clades associated with the biosynthesis of a variety of clinically useful antibiotics and anticancer structural classes were identified in this analysis.

A group of $KS_\beta$ sequence tags of particular interest falls into the clade with $KS_\beta$ genes used in the biosynthesis of anthracycline-type molecules. The anthracyclines doxorubicin and daunorubicin, as discussed above, are both potent anti-cancer agents. Cosmid clones associated with three $KS_\beta$ sequence tags (AZ129, AZ515, TX19) that clade with known anthracycline $KS_\beta$s were recovered from the eDNA libraries, sequenced, annotated and then compared to known anthracycline biosynthetic gene clusters. Two of these clones (AZ129 and TX19) were found to contain gene clusters distinct from any previously described anthracycline gene clusters. The gene cluster captured on the third clone (AZ515) is identical in both gene content and organization to the nogalamycin gene cluster. Sequencing of the TX19 clone revealed two min-PKSs, one containing a $KS_\beta$ gene that clades with type I (21-carbon core) anthracyclines (e.g. doxorubicin, cosmomycin and aclacinomycin) and a second containing a $KS_\beta$ gene with type II (20-carbon core) anthracyclines (e.g. nogalamycin and steffimycin). The gene cluster captured on clone AZ129 is most closely related to the biosynthetic gene cluster encoding for the steffimycin family of anthracyclines, obtained from *Streptomyces steffisburgensis*. However, it contains two additional glycosyltransferases as well as a set of genes predicted to encode for the biosynthesis of aminodeoxy sugars, which are not seen in known steffimycin structures.

The steffimycins are a small subgroup of Type II anthracyclines that has gained only limited attention due to the poor antitumor activity of previously described steffimycin congeners. Extensive structure activity relationship studies within the anthracycline family suggest that interactions mediated by the sugar moiety and the fourth ring of the anthracycline core are likely more critical for determining antitumor potency than the intercalation of DNA by the anthraquinone portion of the anthracycline core. Most clinically relevant anthracyclines contain an aminodeoxy sugar derivative (e.g. L-daunosamine and L-rhodosamine).

To permit heterologous expression studies in *Streptomyces* spp., the AZ129 cosmid was retrofitted with the 6.8 kb DraI fragment from pOJ436 which contains an origin of transfer, an apramycin resistance gene and the ΦC31 phage integration system. Retrofitted AZ129 was then transferred by intergenic conjugation into *Streptomyces albus* to generate *S. albus*/AZ129. In fermentation analyses this strain was found to produce the known steffimycin aglycone biosynthetic intermediate, 8-demethoxy-10-deoxysteffimycinone (4):

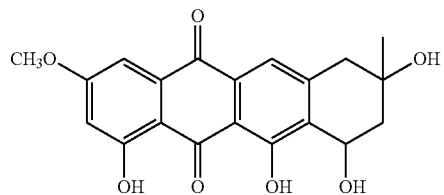

4

The production of an aglycone was expected, as AZ129, like the steffimycin cluster, is missing two key genes (dNDP-D-glucose synthase and a dNDP-D-glucose-4,6-dehydratase) that are required to initiate aminodeoxy sugar biosynthesis. These sugar biosynthesis genes appear in the primary metabolic background of some, but not all, *Streptomyces* spp. The early genes required for deoxy sugar biosynthesis were therefore provided in trans (pIJRham) by cloning the rhamnose biosynthetic operon (oleL, oleS, oleE and eleU) [Rodriguez et al. *J. Mol. Microbiol. Biotech* 2000, 2, 271-276] from oleandromycin biosynthesis under the control of the constitutive ermE* promoter within the conjugative integrative shuttle expression vector pIJ10257 [Hong et al., *J. Biol. Chem.* 2005, 280, 13055-13061] This expression vector utilizes an orthogonal phage integration system (φBT1) and resistance gene (hygromycin) to those present on the retrofitted AZ129 cosmid clone; thereby, allowing for the co-integration of both the biosynthetic gene cluster and the rhamnose biosynthetic operon into distinct chromosomal sites in *S. albus*, yielding *S. albus*/AZ129/pIJRham.

LCMS analysis of organic extracts obtained from cultures of *S. albus*/AZ129/pIJRham showed the presence of three major clone-specific metabolites with masses suggesting the successful addition of either one (MW 544 and 558) or two (MW 756) sugars onto the anthracycline aglycone core. These three metabolites were isolated by $C_{18}$ reversed-phase HPLC from large-scale ethyl acetate extracts as described below. The structures of 1-3, which we have named arimetamycins A, B and C respectively, were determined by HRES-IMS, and extensive 1D and 2D NMR analysis including $^1H$, $^{13}C$, COSY, TOCSY, HMQC, HMBC and ROESY NMR experiments.

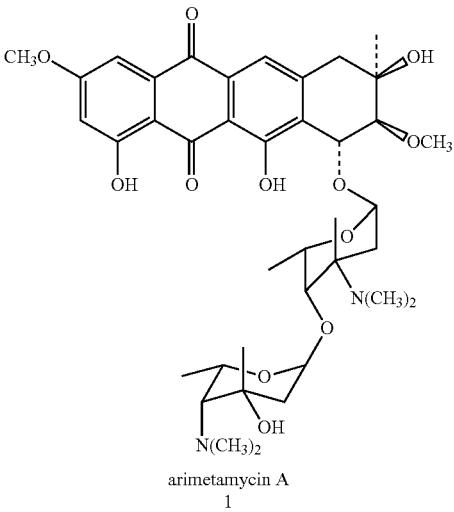

arimetamycin A

1

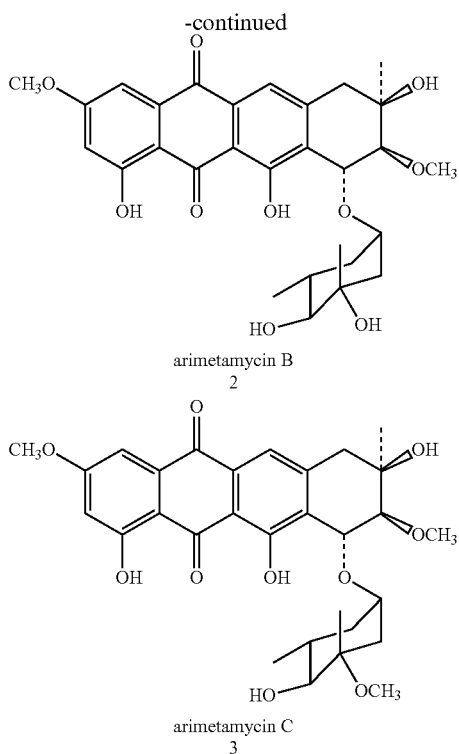

arimetamycin B
2 arimetamycin C
3

The arimetamycins feature a 20-carbon (Type II) anthracycline core with two distinct glycosylation patterns. The disaccharide arimetamycin A (1) contains two uncommon N,N-dimethyl aminodeoxy sugar moieties, brasiliose and 2,6-dideoxy-3-methyl-4-N,N-dimethylamino-L-hexose. Previously described steffimycin family anthracyclines are functionalized with a single rhamnose-based sugar moiety. The monoglycosylated arimetamycins B (2) and C (3) contain L-olivose-based sugars which differ from L-rhamnose by the absence of the C-2' hydroxyl. Arimetamycin B (2) contains an actual L-olivose sugar while arimetamycin C (3) contains a methylated version of this sugar, 3'-OMe-L-olivose.

Arimetamycins A-C (1-3) were evaluated for anticancer activity against representative colon, lung and breast cancer cell lines as described below. The lung cancer line (H69AR) is multidrug resistant (MDR), showing high-level resistance to anthracyclines (50-fold) as well as many other anticancer agents including vincristine, etoposide and mitoxantrone. Arimetamycin A (1) exhibits nanomolar $IC_{50}$ against all cell lines including the H69AR MDR cell line. The monosaccharide functionalized arimetamycins B (2) and C (3) show moderate activity in these cells. The $IC_{50}$ determinations for arimetamycin A are consistently 2-10 fold lower than those observed for either doxorubicin or daunorubicin, and unlike doxorubicin or daunorubicin, arimetamycin A is highly active against both MDR and drug sensitive cell lines. P-glycoprotein expression-dependent MDR is the most clinically significant resistance mechanism affecting the utility of anthracyclines. Compounds of the genus described herein are the first anthracyclines from Streptomyces culture that appear effective against MDR cancers.

To confirm that clone AZ129 contained the full complement of biosynthetic genes comprising an anthracycline biosynthetic gene cluster, we extended the AZ129 eDNA insert by using an overlapping cosmid clone (AZ493) and transformation-associated recombination to produce a bacterial artificial chromosome consisting of eDNA captured on both cosmids (BAC-AZ493AZ129). Following conjugation into S. albus/pIJRham, S. albus(BAC-AZ493AZ129/pIJRham was found to produce the same set of metabolites as S. albus/AZ129/pIJRham, indicating that clone AZ129 contains a complete anthracycline biosynthetic gene cluster spanning roughly 40 kb and containing 36 predicted ORFs. We have named this gene cluster the arm gene cluster (GenBank KF040454).

In one plausible biosynthetic scheme for the arimetamycins, the Type II (C20) anthryacycline 4 is synthesized by nine genes (arm1-9) that show a high sequence identity (67-85%) to their functional counterparts from the steffimycin gene cluster. Intermediate 4 is then available to enter into two distinct glycosylation pathways involving three glycosyltransferases and resulting in the formation of either the disaccharide containing 1 or the monosaccharide containing 2 and 3. The glycocysotranferase arm12, which shows high sequence identity (82%) to the stfG glycocysotranferase from steffimycin biosynthesis, would be expected to transfer the NDP-L-olivose to the common biosynthetic intermediate 4 to generate arimetamycin B (2) and eventually arimetamycin C (3) after methylation by arm14. The two remaining glycosyltransferases found in the arm cluster, arm25 and arm33, do not show significant sequence similarity to any known glycosyltransferases and may incorporate the two aminodeoxy sugars (NDP-brasiliose and NDP-2,6-dideoxy-3-methyl-4-N,N-dimethylamino-L-hexose) seen in arimetamycin A (1). All genes required for the synthesis of these two aminodeoxy sugars, as well as L-olivose, are present in the arm cluster with the exception of the four sugar biosynthesis genes, NDP-D-glucose synthase (oleS), 4,6-dehydratase (oleE), 3,5-epimerase (oleL), and 4-ketoreductase (oleU), which were added in trans.

The preparation of representative compounds of the invention is described in detail below.

Construction of arrayed libraries: The four archived soil eDNA libraries used in this study were constructed according to previously published protocols [S. F. Brady, Nature protocols 2007, 2, 1297-1305.] Briefly, ~100-250 gram aliquots of sifted topsoil were mixed 1:1 (w:v) with lysis buffer (100 mM Tris-HCl, 100 mM EDTA, 1.5 M NaCl, 1% (w/v) CTAB, 2% (w/v) SDS, pH 8.0) and incubated at 70° C. for 2 hrs. Soil debris was then removed from the crude lysate by centrifugation (4,000×g, 30 min). 0.7 volumes of isopropanol was added to the supernatant to precipitate crude eDNA, which was subsequently collected by centrifugation (4,000×g, 30 min). eDNA was separated from the remaining soil particulates by gel electrophoresis (1% agarose gel, 20V, 16 hrs). The high molecular weight DNA compression band was electroeluted from the gel and concentrated using a centrifugal concentrator. Purified eDNA was blunt ended (Epicentre, End-It), ligated into the SmaI site of either pWEB or pWEB-TNC (Epicentre), packaged into lambda phage (Epicentre, MaxPlax) and transfected into E. coli EC100. Each library was expanded to contain at least 10,000,000 unique cosmid clones. Libraries were arrayed as individual pools of approximately 5,000 unique clones, resulting in approximately 2,000 non-redundant pools for each library. Matching glycerol stock and DNA minipreps corresponding to each sub-pool were created to facilitate clone recovery and PCR screening, respectively.

Library screening and phylogenetic analysis of PCR amplicons: DNA aliquots from the 5,000 membered subpools found in each arrayed soil library were screened using degenerate primers designed to amplify min-PKS cassettes containing full-length KS$_\beta$ genes. Each twenty-five μL PCR reaction contained 50 ng of cosmid DNA, 2.5 μM of each primer (dp:KS$_\alpha$-TTCGGSGGITTCCAGWSIGCSATG and dp:ACP-TCSAKSAGSGCSAISGASTCGTAICC), 2 mM dNTPs, 1× ThermoPol reaction buffer (New England Biolabs), 0.5 units Taq DNA polymerase and 5% DMSO. PCR was conducted using the following touchdown protocol: denaturation (95° C., 2 min), 8 touchdown cycles [95° C., 45 s; 65° C. (−1° C. per cycle), 1 min; 72° C., 2 min], 35 standard cycles (95° C., 45 s; 58° C., 1 min; 72° C., 2 min), and a final extension step (72° C., 2 min) The resulting PCR amplicons were gel-purified and sequenced. 400 by KS$_\beta$ gene fragments (corresponding to nucleotides 252-652 of DpsB) from each amplicon were aligned using ClustalW. The pairwise distances (p-distance) between eDNA-derived KS$_\beta$ sequences and KS$_\beta$ sequences from gene clusters encoding for known medicinally relevant aromatic polyketides were calculated using MEGA5.1. [K. Tamura, D. Peterson, N. Peterson, G. Stecher, M. Nei, S. Kumar, *Molecular biology and evolution* 2011, 28, 2731-2739]. eDNA-derived KS$_\beta$ sequences that fell within a p-distance of 0.3 to a KS$_\beta$ from a medicinally relevant metabolite were used to generate sub-trees. One thousand bootstrap replicates were used to evaluate the robustness of branches in each neighbor-joining tree. The final tree was constructed with the eDNA-derived KS$_\beta$ sequences that formed well-supported clades with the KS$_\beta$ sequences of medicinally relevant metabolites.

Clone recovery and bioinformatics analysis of recovered gene clusters: eDNA clones (AZ129, AZ515 and TX19) containing KS$_\beta$ sequences that formed well-supported clades with KS$_\beta$ sequences from the biosynthesis of known anthracyclines were recovered from eDNA libraries by dilution PCR screening of the respective sub-pools from which they were identified. To accomplish this, overnight cultures of each sub-pool were plated into 96-well microtiter plates at a dilution of $10^{-5}$ or $10^{-6}$. After 18 hrs at 37° C., the diluted cultures were screened by whole-cell PCR using the KS$_\beta$ screening primers and touch-down PCR protocol described above. PCR positive wells were plated onto solid media to yield distinct colonies that were screened in a second round of whole-cell PCR. The recovered cosmids were sequenced by 454-pyrosequencing and named after the specific library sub-pools from which they were isolated (e.g. AZ129, AZ515 and TX19). Open reading frame predictions were carried out using MetaGeneMark [W. Zhu, A. Lomsadze, M. Borodovsky, *Nucleic Acids Research* 2010, 38, e132], and predicted open reading frames were annotated based on Blast search results. eDNA-derived gene clusters were compared manually to previously reported gene clusters for the biosynthesis of doxorubicin/daunorubicin (GeneBank Accession No.: L35560), aclacinomycin (AF257324), cosmomycin (ABC00728), nogalamycin (AJ224512) and steffimycin (AM156932).

Heterologous expression and cloning of the rhamnose biosynthetic genes: To permit the shuttling of cosmid AZ129 into *Streptomyces* spp. for heterologous expression studies, cosmid AZ129 was digested with PsiI and then ligated with the 6.81 kb DraI fragment of pOJ436 [M. Bierman, R. Logan, K. O'Brien, E. T. Seno, R. N. Rao, B. E. Schoner, *Gene* 1992, 116, 43-49] that contains an origin of transfer (oriT), an apramycin resistance gene [aac (3)IV], and the φC31-based integration system. Using *E. coli* S17.1 as a donor strain, the retrofitted cosmid was transferred into *Streptomyces albus* by intergenic conjugation to yield *S. albus*/AZ129. The rhamnose biosynthetic operon (oleL: dNDP-4-keto-6-deoxyglucose 3,5-epimerase, oleS: dNDP-D-glucose synthase, oleE: dNDP-glucose 4,6-dehydratase and oleU: dNDP-4-keto-hexulose reductase) was amplified from pRHAM [L. Rodriguez, C. Oelkers, I. Aguirrezabalaga, A. F. Brana, J. Rohr, C. Mendez, J. A. Salas, *Journal of molecular microbiology and biotechnology* 2000, 2, 271-276] using the forward primer 5'-ATCG<u>CATATG</u>GAGTTACTCGACGTCGACGGGG-3' and the reverse primer 5'-ATCG <u>TTAATTAA</u>TCATGCTGCTCCTCGCCGGGTCGGT-3' [restriction sites added for cloning purposes (NdeI and PacI, respectively) are underlined]. The resulting amplicon was digested with NdeI/PacI and cloned in front of the ermE* promoter in the shuttle expression vector pIJ10257 to give pIJRham. pIJRham was transformed into *E. coli* S17.1 and then shuttled into *S. albus*/AZ129 by intergenic conjugation to generate *S. albus*/AZ129/pIJRham.

Extraction and Isolation of clone-specific metabolites: Compound 4 was isolated from cultures of *S. albus*/AZ129 grown (200 rpm at 30° C.) in 125 mL baffled flasks containing 50 mL of R5A media. Seven days old cultures were extracted with ethyl acetate (3:1 v/v). The resulting extract was subjected to isocratic (65% aqueous, 35% acetonitrile containing 0.1% trifluoroacetic acid) reversed-phase HPLC (C$_{18}$, 10 mm×250 mm, 3.5 mL/min) to afford 0.5 mg of 4 per 100 mL of culture broth. The structure of 4 was determined by HRESIMS (369.0976 [M−H]$^-$; 369.0974 calcd for C$_{20}$H$_{17}$O$_7$) and 1D and 2D NMR data to be the previously described steffimycin biosynthetic intermediate 8-demethoxy-10-deoxystef-fimycinone.

Arimetamycins A (1), B (2) and C (3) were isolated from cultures of *S. albus*/AZ129/pIJRham. 125 mL baffled flasks containing 50 ml of R5A were inoculated with *S. albus*/AZ129/pIJRham spore stocks. After seven days of shaking (200 rpm at 30° C.), cultures were extracted with ethyl acetate (EtOAc, 3:1 v/v) and concentrated in vacuo. Arimetamycins A (1), B (2) and C (3) were isolated from the EtOAc extract using two rounds of reversed-phase HPLC (C$_{18}$ column, 10 mm×250 mm, 3.5 mL/min). The first round of HPLC using 35% acetonitrile with 0.1% trifluoroacetic acid yielded three crude samples, which were re-purified by the second round of HPLC using 60%, 70% and 80% methanol with 0.1% trifluoroacetic acid to yield arimetamycins A (1, 2.5 mg/L), B (2, 0.5 mg/L) and C (3, 3 mg/L), respectively. Arimetamycin A (1): red gum; [α]$^{25}_D$+15 (c 0.2, MeOH); UV (MeOH) λ$_{max}$ 230, 270, 289, 445 nm; IR (neat) ν$_{max}$ 3200, 3073, 2990, 2852, 2118, 1673, 1625, 1568 cm$^{-1}$; $^1$H and $^{13}$C NMR, COSY, and HMBC were also obtained; HRESIMS m/z 757.3553 [M+H]$^+$ (cacld for C$_{39}$H$_{52}$N$_2$O$_{13}$, 757.3548).

Arimetamycin B (2): red powder; [α]$^{25}_D$+37 (c 0.1, MeOH); UV (MeOH) λ$_{max}$ 229, 270, 290, 446 nm; IR (neat) λ$_{max}$ 3404, 3092, 2929, 2056, 1678, 1610 cm$^{-1}$; $^1$H and $^{13}$C NMR were also obtained; HRESIMS m/z 543.1479 [M−H]$^-$ (cacld for C$_{27}$H$_{27}$O$_{12}$, 543.1503).

Arimetamycin C (3): red powder; [α]$^{25}_D$+83 (c 0.2, MeOH); UV (MeOH)) λ$_{max}$ 229, 270, 290, 446 nm; IR (neat) ν$_{max}$ 3272, 3084, 2932, 2854, 2109, 1707, 1677, 1623, 1565 cm$^{-1}$; $^1$H and $^{13}$C NMR, COSY, and HMBC also obtained; HRESIMS m/z 557.1665 [M−H]$^-$ (cacld for C$_{28}$H$_{29}$O$_{12}$, 557.1659). Other species in the genus I may be obtained analogously by inserting the appropriate gene for the desired transformation. FIG. 1 outlines the genes that may be inserted to produce the desired species.

Compounds were tested in HTC 116 cell line, which is an art-recognized isogenic human disease model predictive of activity in human patients. They were tested according to the following standard protocol:

Antiproliferative assay: The cytotoxicities of arimetamycins A (1), B (2) and C (3) were evaluated using four human cancer cell lines: HCT-116 colon carcinoma (ATCC; CCL-247) [M. G. Brattain, W. D. Fine, F. M. Khaled, J. Thompson, D. E. Brattain, *Cancer Res* 1981, 41, 1751-1756], WiDr colorectal adenocarcinoma (ATCC; CCL-218) [P. Noguchi, R. Wallace, J. Johnson, E. M. Earley, S. O'Brien, S. Ferrone, M. A. Pellegrino, J. Milstien, C. Needy, W. Browne, J. Petricciani, In vitro 1979, 15, 401-408], MDR-MB-231 breast adenocarcinoma (ATCC; HTB-26) [B. R. Brinkley, P. T. Beall, L. J. Wible, M. L. Mace, D. S. Turner, R. M. Cailleau, Cancer Res 1980, 40, 3118-3129] and H69AR multidrug resistant lung carcinoma (ATCC; CRL-11351) [S. E. Mirski, J. H. Gerlach, S. P. Cole, Cancer Res 1987, 47, 2594-2598] cell lines. HCT-116 and H69AR cells were grown in McCoy's 5A Modified Medium (Gibco) supplemented with 10% (v/v) FBS and RPMI-1640 (ATCC) supplemented with 20% (v/v) FBS, respectively. WiDr and MDA-MB-231 cells were grown in DMEM Medium (Gibco) supplemented with 10% (v/v) FBS. All the cell lines were incubated at 37° C. with 5% $CO_2$. Cells in log phase growth were harvested by trypsinization. Cells were seeded into 96-well plates (HCT-116: 1,000 cells/well, WiDr: 3,000 cells/well, MDA-MB-231: 8,000 cells/well, H69AR: 25,000 cells/well) and incubated overnight at 37° C. with 5% $CO_2$. Compounds 1-3 (in DMSO) were sequentially diluted (3-fold starting at 50 μg/mL) across a 96-well plate and 100 μL was transferred to the appropriate wells in the assay plates. Doxorubicin (Sigma-Aldrich) and daunorubicin (Sigma-Aldrich) were used as positive controls and DMSO was used as a negative control. The plates were incubated at 37° C. for 3-6 days depending on the growth rate and then evaluated for viability using either an MTT (3-(4,5-Dimethylthiazol-2-yl)-2,5-diphenyltetrazolium bromide) (MDR-MB-231 and H69AR) or crystal violet (HCT-116 and WiDr) based colorimetric assay [R. Supino, Methods in molecular biology 1995, 43, 137-149; bD. Zivadinovic, B. Gametchu, C. S. Watson, Breast Cancer Res 2005, 7, R101-112]. Cell viability is recorded based on the percent stain present in each well relative to no drug DMSO control wells. Assays were run in triplicate.

Confirmatory tests may be run in other cancer cell models. For example, SW480 and DLD-1 human colorectal cancer; A549 human lung cancer; AGS human gastric cancer; HepG2 human liver cancer; and MCF-7 human breast cancer cell lines can be obtained from the American Type Culture Collection (Rockville, Md.).

Results of testing of exemplary compounds of the invention are shown in the following table:

| Compound | $IC_{50}$((nM)) | | | |
|---|---|---|---|---|
| Cell line<br>Cancer | HCT116<br>Colon | WiDr<br>Colon | MDSMB231<br>Breast | H69AR<br>Lung/MDR |
| Arimetamycin A(1) | 2.5 | 0.5 | 164 | 67 |
| Arimetamycin B(2) | 1800 | 7500 | 29600 | 47100 |
| Arimetamycin C(3) | 1400 | 5200 | 27700 | 18800 |
| Doxorubicin | 22.5 | 30.9 | 970 | 18400 |
| Daunorubicin | 6.8 | 5.5 | 330 | 4800 |

While it may be possible for the compounds described herein to be administered to patients as the raw chemical, it is usually desirable to present them as a pharmaceutical composition. According to a further aspect, the present invention provides a pharmaceutical composition comprising a compound together with one or more pharmaceutical carriers and optionally one or more other therapeutic ingredients. The carrier(s) must be "acceptable" in the sense of being compatible with the other ingredients of the formulation and not deleterious to the recipient thereof.

The formulations for administration to patients include those suitable for oral, parenteral (including subcutaneous, intradermal, intramuscular, intravenous and intraarticular), rectal and topical (including dermal, buccal, sublingual and intraocular) administration. In most cases, parenteral administration will be preferred. The most suitable route may depend upon the condition and disorder of the recipient. The formulations may conveniently be presented in unit dosage form and may be prepared by any of the methods well known in the art of pharmacy.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

The invention claimed is:

1. A compound of formula:

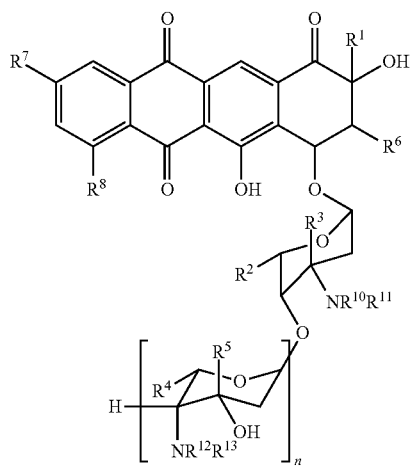

wherein
$R^1$ is chosen from methyl, acetyl and hydroxyacetyl;
$R^2$-$R^5$ and $R^{10}$-$R^{13}$ are independently chosen from H and methyl;
$R^6$ is chosen from OH and $OCH_3$;
$R^7$ and $R^8$ are independently chosen from H, OH and $OCH_3$; and
n is zero or one.

2. A compound according to claim 1 wherein $R^7$ is OH.
3. A compound according to claim 1 wherein $R^7$ is $OCH_3$.
4. A compound according to claim 1 wherein $R^6$ is $OCH_3$.
5. A compound according to claim 1 wherein $R^8$ is H.
6. A compound according to claim 1 wherein $R^8$ is OH.
7. A compound according to claim 6 wherein $R^6$ is $OCH_3$.
8. A compound according to claim 7 wherein $R^7$ is $OCH_3$.
9. A compound according to claim 1 wherein n is one and all of $R^2$-$R^5$ and $R^{10}$-$R^{13}$ are methyl.
10. A compound according to claim 9 wherein n is one and all of $R^2$-$R^5$ and $R^{10}$-$R^{13}$ are methyl.
11. A compound according to claim 9 wherein $R^1$ is methyl.
12. A compound according to claim 10 wherein $R^1$ is methyl.
13. A compound according to claim 9 wherein $R^1$ is acetyl.
14. A compound according to claim 10 wherein $R^1$ is acetyl.
15. A compound according to claim 9 wherein $R^1$ is hydroxyacetyl.
16. A compound according to claim 10 wherein $R^1$ is hydroxyacetyl.
17. A method for treating cancer comprising administering to a patient diagnosed with cancer, a therapeutically effective amount of a compound according to claim 1.
18. A pharmaceutical composition comprising a pharmaceutically acceptable carrier and a compound according to claim 1.

* * * * *

UNITED STATES PATENT AND TRADEMARK OFFICE
CERTIFICATE OF CORRECTION

PATENT NO. : 9,217,008 B1  
APPLICATION NO. : 14/327597  
DATED : December 22, 2015  
INVENTOR(S) : Brady et al.

Page 1 of 1

It is certified that error appears in the above-identified patent and that said Letters Patent is hereby corrected as shown below:

IN THE CLAIMS

Column 16, Line 37: Claim 10, Delete "Claim 9" and insert -- Claim 8 --

Signed and Sealed this  
Fifth Day of April, 2016

Michelle K. Lee  
*Director of the United States Patent and Trademark Office*

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (6)..(6)
<223> OTHER INFORMATION: n can be c or g
<220> FEATURE:

```
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (16)..(16)
<223> OTHER INFORMATION: n can be a or t
<220> FEATURE:
<221> NAME/KEY: misc_feature
<222> LOCATION: (17)..(17)
<223> OTHER INFORMATION: n can be c or g
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n can be c or g

<400> SEQUENCE: 1
ttcggnggnt tccagnnngc natg                                           24

<210> SEQ ID NO 2
<211> LENGTH: 26
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (3)..(3)
<223> OTHER INFORMATION: n can be c or g
<220> FEATURE:
<221> NAME/KEY: misc_feature
<222> LOCATION: (5)..(5)
<223> OTHER INFORMATION: n can be t or g
<220> FEATURE:
<221> NAME/KEY: misc_feature
<222> LOCATION: (6)..(6)
<223> OTHER INFORMATION: n can be c or g
<220> FEATURE:
<221> NAME/KEY: misc_feature
<222> LOCATION: (9)..(9)
<223> OTHER INFORMATION: n can be c or g
<220> FEATURE:
<221> NAME/KEY: misc_feature
<222> LOCATION: (12)..(12)
<223> OTHER INFORMATION: n can be c or g
<220> FEATURE:
<221> NAME/KEY: modified_base
<222> LOCATION: (14)..(14)
<223> OTHER INFORMATION: I
<220> FEATURE:
<221> NAME/KEY: misc_feature
<222> LOCATION: (15)..(15)
<223> OTHER INFORMATION: n can be c or g
<220> FEATURE:
<221> NAME/KEY: misc_feature
<222> LOCATION: (18)..(18)
<223> OTHER INFORMATION: n can be c or g
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or t
```

```
<400> SEQUENCE: 2
tcnannagng cnanngantc gtancc                                    26

<210> SEQ ID NO 3
<211> LENGTH: 32
<212> TYPE: DNA
<213> ORGANISM: Artificial Sequence
<220> FEATURE:
<223> OTHER INFORMATION: synthetic primer

<400> SEQUENCE: 3
atcgcatatg gagttactcg acgtcgacgg gg                             32

<210> SEQ ID NO 4
<211> LENGTH: 37
<212> TYPE: DNA
<213> ORGANISM: Artificial Sequence
<220> FEATURE:
<223> OTHER INFORMATION: synthetic primer

<400> SEQUENCE: 4
atcgttaatt aatcatgctg ctcctcgccg ggtcggt                        37
```